(12) United States Patent
Um

(10) Patent No.: US 11,359,030 B2
(45) Date of Patent: Jun. 14, 2022

(54) METHOD FOR PREPARING LOW MOLECULAR WEIGHT HYALURONIC ACID

(71) Applicant: YOUREH CO., LTD., Seoul (KR)

(72) Inventor: Hyang Mae Um, Seoul (KR)

(73) Assignee: YOUREH CO., LTD., Seoul (KR)

( * ) Notice: Subject to any disclaimer, the term of this patent is extended or adjusted under 35 U.S.C. 154(b) by 0 days.

(21) Appl. No.: 16/495,617

(22) PCT Filed: Apr. 9, 2018

(86) PCT No.: PCT/KR2018/004127
§ 371 (c)(1),
(2) Date: Sep. 19, 2019

(87) PCT Pub. No.: WO2018/186720
PCT Pub. Date: Oct. 11, 2018

(65) Prior Publication Data
US 2020/0095344 A1 Mar. 26, 2020

(30) Foreign Application Priority Data

Apr. 7, 2017 (KR) .................. 10-2017-0045342

(51) Int. Cl.
*C08B 37/08* (2006.01)
(52) U.S. Cl.
CPC ................. *C08B 37/0072* (2013.01)
(58) Field of Classification Search
CPC ........... C08B 37/0072; C08B 37/0069; C08B 37/0003
See application file for complete search history.

(56) References Cited

U.S. PATENT DOCUMENTS

| 8,829,180 B2 * | 9/2014 | Yoshida | .............. | C08B 37/0003 |
| | | | | 536/53 |
| 2009/0215719 A1 * | 8/2009 | Yoshida | ................. | A61K 8/735 |
| | | | | 514/54 |

FOREIGN PATENT DOCUMENTS

| JP | S6357602 A | | 3/1988 | |
| JP | 5077681 B | * | 10/1993 | ............. C08B 37/08 |
| KR | 20070000057 A | | 1/2007 | |
| KR | 20080002848 A | | 1/2008 | |
| KR | 20100079362 A | | 7/2010 | |
| KR | 20130078829 A | | 7/2013 | |
| KR | 20130128655 A | | 11/2013 | |
| KR | 20150064454 A | | 6/2015 | |

OTHER PUBLICATIONS

Aviva Shiedlin et al., "Evaluation of Hyaluronan from Different Sources: *Streptococcus zooepidemicus*, Rooster Comb, Bovine Viteous, and Human Umbilical Cord," Biomacromolecules, 5, 2122-2127 (2004).
Barrie Fong Chong et al., "Microbial hyaluronic acid production," Appl. Microbiol. Biotechnol. 66: 341-351 (2005).
B.J. Parsons, "Chemical aspects of free radical reactions in connective tissue," Free Radical Damage and its Control, 281-300, Elsevier Science B.V. (1994).
Noriko Motohashi et al., "Analysis by High-Performance Gel Permeation Chromatography of Hyaluronic Acid in Animal Skins and Rabbit Synovial Fluid," Journal of Chromatogrphy, 435, pp. 335-342 (1988).
Vellarkad N. Viswanadhan et al., "Configurational statistics of C(4)-C(8) linked polymers of (+)-catechin or (−)-epicatechin with mixed axial/equatorial substituents at C(2)," Int. J. Biol. Macromol., vol. 10 (Feb. 1988).

* cited by examiner

*Primary Examiner* — Pancham Bakshi
(74) *Attorney, Agent, or Firm* — Miles & Stockbridge P.C.

(57) ABSTRACT

The present invention relates to a method for preparing low molecular weight hyaluronic acid having a molecular weight of 100,000 to 200,000 daltons, the method comprising heating treatment, in the pH range 2.5 to 3.5, for an aqueous solution that contains hyaluronic acid having a molecular weight of 500,000 daltons or greater.

5 Claims, 7 Drawing Sheets

METHOD FOR PREPARING LOW MOLECULAR WEIGHT HYALURONIC ACID

PRIORITY INFORMATION

The present application is a national stage filing under 35 U.S.C. § 371 of PCT/KR2018/004127, filed on Apr. 9, 2018 which claims priority to KR Application No. 10-2017-0045342 filed on Apr. 7, 2017. The applications are incorporated herein by reference in their entirety.

TECHNICAL FIELD

The present invention relates to a method of preparing hyaluronic acid having a molecular weight range within which excellent skin permeation and moisturizing effects can be realized.

BACKGROUND ART

Hyaluronic acid, basic units of which are D-glucuronic acid and N-acetyl-D-glucosamine, has a molecular weight ranging from hundreds of thousands to millions of Daltons. Such hyaluronic acid is a linear polymer which is present in the same structure in almost all living organisms, and mainly constitutes an extracellular matrix. Since hyaluronic acid has the same structure without differences between species, it is known that it has no immune response regardless of origins thereof. Hyaluronic acid is a safe natural polysaccharide used in many fields, such as degenerative arthritis treatment, cataract treatment, wrinkle improvement, drug delivery, stem cell supports, and cosmetic moisturizing and maintenance ingredients, to date. Hyaluronic acid, as a polymer, has a high density as the molecular weight thereof increases, thus having higher viscosity.

In the beginning, hyaluronic acid was extracted from chicken combs and was industrially used in medicine, cosmetics, foods, and the like [Biomacromolecules, 5, 2122-2127 (2004)]. Recently, hyaluronic acid is mainly produced using fermentation methods using microorganisms due to the fear of infectious diseases, such as bird flu, which can be contracted from animals [Appl. Microbiol. Biotechnol. 66(4): 341-51 (2005)].

The amount of hyaluronic acid in human skin has been reported to decrease with age, which is considered to be one of direct causes of decreased skin elasticity and water content [In: Free radical Damage and Its control, 281-300, Elsevier Science (1994)].

Hyaluronic acid is widely used as a moisturizer for cosmetics because it is easily dissolved in water and retains a lot of moisture in a molecular structure thereof. In addition, hyaluronic acid is applied to creams for burns and wounds, injections, gauze, and the like, and is used as a formulation for protecting the inside of the cornea. Further, hyaluronic acid has been used for the manufacture of porous sponge-like matrices used in wound coating materials and dental matrices in tissue engineering.

However, hyaluronic acid, which is extracted from animal tissues or produced by fermentation, does not generally penetrate the skin because it is a polymer polysaccharide with a molecular weight of 500,000 Daltons or greater which has a high polymerization degree. That is, when hyaluronic acid having a molecular weight of 500,000 Daltons or greater is applied to the skin, it can prevent evaporation of water from the skin due to its ability to absorb moisture in the air, but it stays on a surface of the skin and is easily washed off from the skin surface upon washing because it cannot penetrate the skin. Accordingly, it is difficult to sustain a skin moisturizing effect. On the other hand, hyaluronic acid having a molecular weight of 100,000 Daltons or less can penetrate the skin, but it lacks the property to contain moisture due to low molecular weight thereof, so that moisturizing effect is not sustained.

In addition, hyaluronic acid having a molecular weight of 20,000 Daltons or less is known to effectively penetrate the skin, but induces a pro-inflammatory response because it binds with toll-like receptors 2 and 4, receptors on macrophages in the skin, to initiate an immune response.

As methods of reducing the molecular weight of hyaluronic acid, a method of using gamma rays, ultrasonic waves, or ultraviolet light (Journal of Chromatography, 435, pp335-342, 1988; Int. Biol. Macrmol., p10,1988), a method using an acid or a base catalyst (Japanese Patent Application Publication No. S63-57602), a method of using a microfluidizer, and the like are known. However, such known methods are used to prepare hyaluronic acid having a molecular weight of 100,000 Daltons or less. That is, no effective method of preparing hyaluronic acid having direct skin permeation effect or a molecular weight that allows absorption and moisture retention has yet been proposed.

DISCLOSURE

Technical Problem

Therefore, the present invention has been made in view of the above problems, and it is one object of the present invention to provide a method of effectively preparing low-molecular weight hyaluronic acid that is capable of penetrating the skin and maintaining optimal wetting conditions, more particularly, a method of preparing low-molecular weight hyaluronic acid that does not exhibit the disadvantages of not penetrating into the stratum corneum of the skin and being washed off, thus not providing a long-term moisturizing effect to the skin, while exhibiting moisturizing effect of hyaluronic acid having a molecular weight of 500,000 Daltons or greater used as a raw material for existing cosmetics and the like.

Technical Solution

Means for solving the above problems in the present invention are as follows:

1. In accordance with an aspect of the present invention, the above and other objects can be accomplished by the provision of a method of preparing low-molecular weight hyaluronic acid having a molecular weight of 100,000 to 200,000 Daltons, the method including: thermally treating, in a range of pH 2.5 to 3.5, an aqueous solution that contains hyaluronic acid having a molecular weight of 500,000 Daltons or greater.

2. A concentration of the aqueous solution may be 1 to 2% (weight/volume).

3. The thermally treating may be performed at 80 to 90° C.

4. The thermally treating may be performed for 15 to 30 minutes.

5. After the thermally treating, a resultant reaction solution may be neutralized with an aqueous alkali metal hydroxide solution to obtain low-molecular weight hyaluronic acid in a form of an alkali metal salt.

6. The alkali metal salt may be a sodium salt.

7. After the neutralization, an organic solvent may be added to the reaction solution to generate a precipitate, and the precipitate may be filtered to obtain a powder-type alkali metal salt of hyaluronic acid.

8. The organic solvent may be one or more selected from the group consisting of methanol, ethanol, acetone, and isopropyl alcohol.

9. The organic solvent may be added in a volume ratio of 1:5 to 1:6 based on the reaction solution.

Advantageous Effects

As apparent from the above description, the present invention provides a complex steps-omitted and simplified method of preparing hyaluronic acid having a molecular weight of 100 to 200 kDa which does not exhibit a skin permeation problem, which is a disadvantage of existing hyaluronic acid used as a raw material for cosmetics, and is capable of maintaining maximum moisturizing power as well as skin permeation. Low-molecular weight hyaluronic acid prepared according to the method of the present invention is suitable for use in cosmetics and medicinal and medical compositions because it can penetrate the skin and maintain a maximally moisturized state to alleviate atopic symptoms.

BEST MODE

Figure 1:
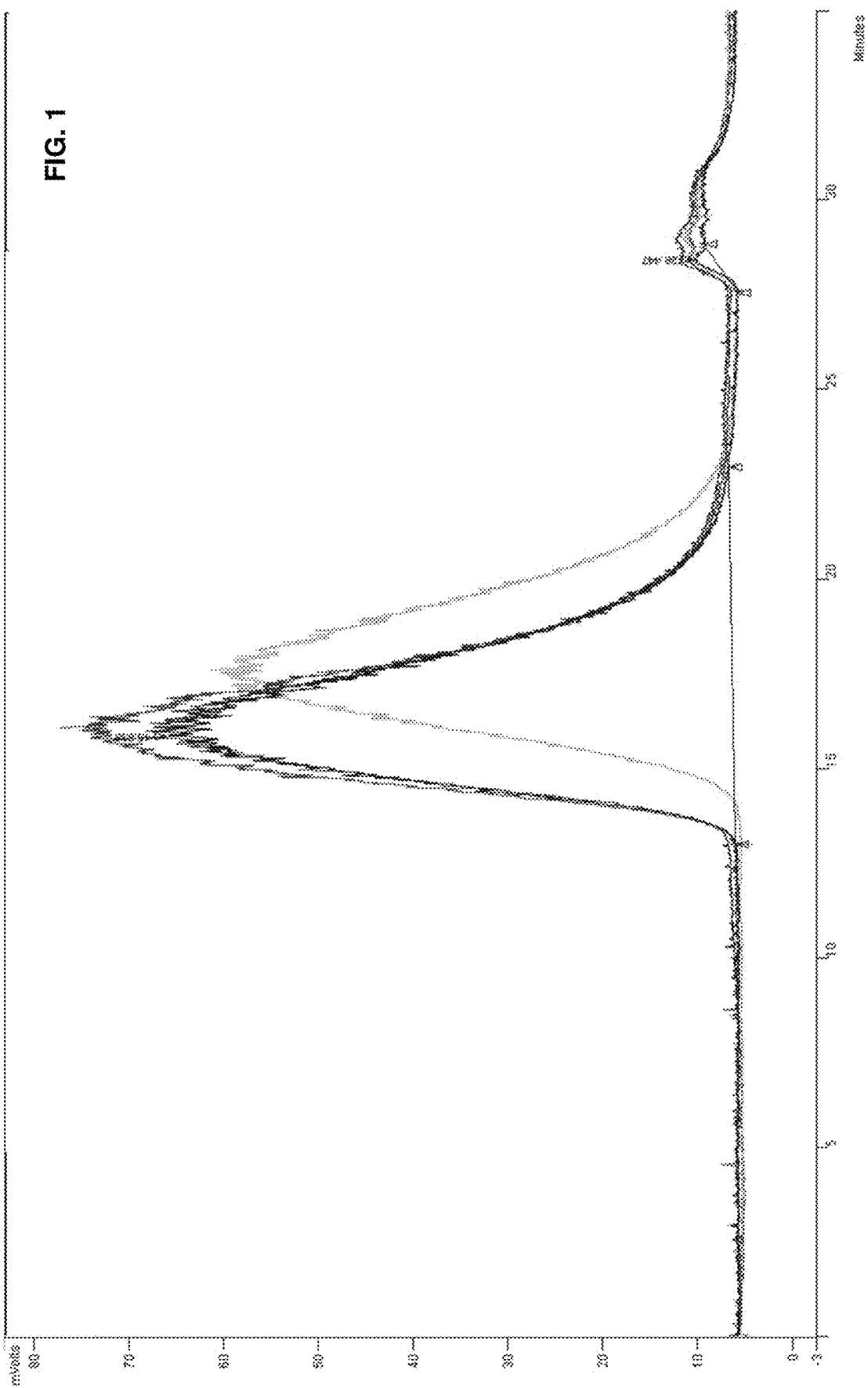
FIG. 1 is an HPLC chromatogram illustrating a molecular weight distribution of low-molecular weight sodium hyaluronate prepared according to each of Examples 1 to 3 (blue: a standard molecular weight of 200,000 Daltons, red: Example 1, green: Example 2, black: Example 3).

The present invention relates to a method of preparing low-molecular weight hyaluronic acid having a molecular weight of 100,000 to 200,000 Daltons, the method including thermally treating, in a range of pH 2.5 to 3.5, an aqueous solution that contains hyaluronic acid having a molecular weight of 500,000 Daltons or greater.

In the present invention, examples of hyaluronic acid having a molecular weight of 500,000 to 3,000,000 Daltons, which is used as a starting material, may include hyaluronic acid having an average molecular weight grade of 500,000 Daltons which is generally used as a cosmetic material, hyaluronic acid having a molecular weight grade of 1,000,000 Daltons which is used as a pharmaceutical raw material, and hyaluronic acid having a molecular weight grade of 3,000,000 Daltons. In general, it is preferred to use hyaluronic acid having an average molecular weight of 500,000 Daltons which is a raw material for cosmetics, but the present invention is not limited thereto.

The aqueous solution may be prepared by dissolving hyaluronic acid having a molecular weight of 500,000 to 3,000,000 Daltons in water, preferably by dissolving in distilled water at a concentration of 1 to 2% (weight/volume). Here, the acid may be any acid, such as hydrochloric acid, phosphoric acid, or acetic acid, generally used in the field to the present invention pertains.

The thermal treatment process is preferably performed at 80 to 90° C. for process efficiency. In addition, the thermal treatment process is preferably performed for 15 to 30 minutes depending upon the type of a raw material used as a starting material.

In the present invention, pH of the aqueous solution containing hyaluronic acid that has a molecular weight of 500,000 Daltons or greater is adjusted to 2.5 to 3.5, and the thermal treatment process is performed at the above temperature for the above time, thereby obtaining hyaluronic acid having an average molecular weight of 100,000 to 200,000 Daltons.

In the present invention, after the thermal treatment process, the reaction solution may be neutralized with a base, preferably an aqueous alkali metal hydroxide solution, thereby obtaining low-molecular weight hyaluronic acid in the form of an alkali metal salt. In this case, pH of the reaction solution is adjusted to 6.5 or higher, preferably 6.5 to 7.0. The alkali metal hydroxide may be sodium hydroxide. In this case, a sodium salt of low-molecular weight hyaluronic acid may be obtained.

A metal salt of low-molecular weight hyaluronic acid prepared according to the aforementioned method may be obtained in the form of a powder-type alkali metal salt of low-molecular weight hyaluronic acid by adding an organic solvent to a reaction solution thereof to form a precipitate and filtering the same. The organic solvent may be one or more selected from the group consisting of methanol, ethanol, acetone, and isopropyl alcohol, and may be added in a volume ratio of 1:5 to 1:6 based on the reaction solution.

EXAMPLES

Hereinafter, the present invention will be described in more detail with reference to the following examples. However, the examples presented below are only examples for carrying out the present invention, and the scope of the present invention is not limited to the scope of these examples.

1. Optimization of Preparation Conditions of Low-Molecular Weight Sodium Hyaluronate

Example 1

1 g of commercially available cosmetic-grade sodium hyaluronate (manufactured by Bloomage Freda Biopharm., molecular weight: 500,000 to 1200,000 Daltons) was dissolved in 100 ml of distilled water to prepare an aqueous 1.0% (w/v) solution. 0.58 ml of 4 N HCl was added to the 1.0% (w/v) aqueous solution to adjust pH thereof to 2.5, followed by heating in 90° C. water for 15 minutes. Next, the temperature of the heated mixture was lowered to room temperature in cold water, and then a 4 N NaOH solution was added thereto to adjust pH thereof to 6.5, followed by adding 400 ml of anhydrous ethanol thereto such that a precipitate was generated. The generated precipitate was filtered, and then dried at 50° C., thereby obtaining 8.9 g of sodium hyaluronate.

Example 2

An experiment was carried out in the same manner as in Example 1, except that heating was performed in 90° C. water for 30 minutes. As a result, 8.7 g of sodium hyaluronate was obtained.

Example 3

An experiment was carried out in the same manner as in Example 1, except that 0.23 ml of a 4 N HCl solution was added to an aqueous sodium hyaluronate solution to adjust pH thereof to 3.5, and heating was performed in 90° C. water for 30 minutes. As a result, 9.1 g of sodium hyaluronate was obtained.

FIG. 1 shows that an average molecular weight of sodium hyaluronate obtained according to each of Example 1 (red peak) and Example 3 (black peak) overlaps a standard molecular weight (blue peak) of 200,000 Daltons, and a molecular weight of sodium hyaluronate obtained according to Example 2 (green peak) is less than 200,000 Daltons (blue peak).

Example 4

An experiment was carried out in the same manner as in Example 1, except that 0.21 ml of a 4 N HCl solution was added to an aqueous sodium hyaluronate solution to adjust pH thereof to 3.0. As a result, 8.9 g of sodium hyaluronate was obtained.

Example 5

An experiment was carried out in the same manner as in Example 1, except that 0.21 ml of a 4 N HCl solution was added to an aqueous sodium hyaluronate solution to adjust pH thereof to 3.0, and heating was performed in 90° C. water for 30 minutes. As a result, 8.2 g of sodium hyaluronate was obtained.

Figure 2:
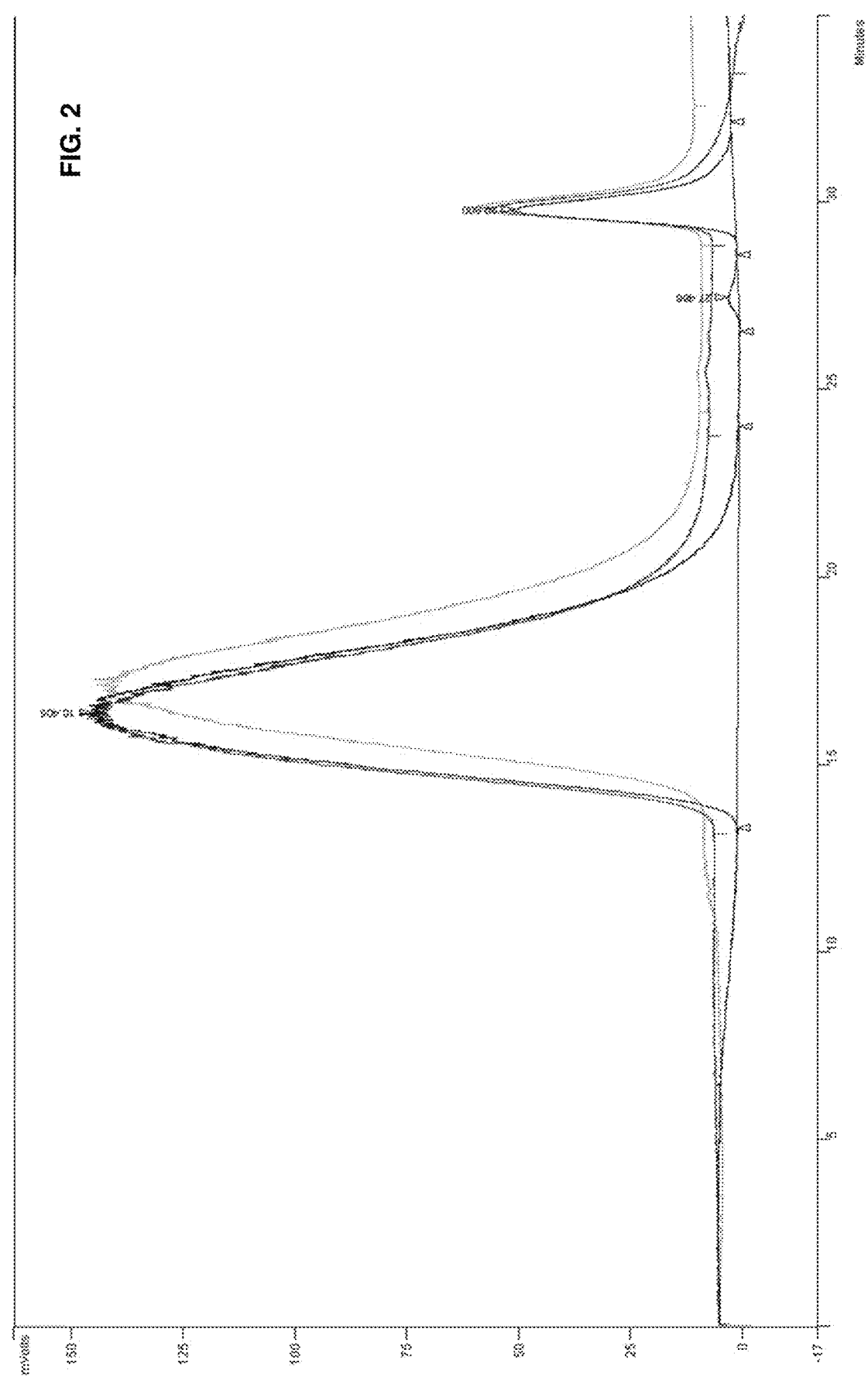
FIG. 2 is an HPLC chromatogram illustrating a molecular weight distribution of low-molecular weight sodium hyaluronate prepared according to each of Examples 4 and 5 (blue: a standard molecular weight of 200,000 Daltons, red: Example 4, green: Example 5).

FIG. 2 shows that an average molecular weight of sodium hyaluronate obtained according to Example 4 (red peak) overlaps a standard molecular weight of 200,000 Daltons, and a molecular weight of sodium hyaluronate obtained according to Example 5 (green peak) is smaller than a standard molecular weight of 200,000 Daltons (blue peak).

Example 6

An experiment was carried out in the same manner as in Example 1, except that 0.21 ml of a 4 N HCl solution was added to an aqueous sodium hyaluronate solution to adjust pH thereof to 3.0, and heating was performed in 80° C. water for 15 minutes. As a result, 8.7 g of sodium hyaluronate was obtained.

Example 7

An experiment was carried out in the same manner as in Example 1, except that 0.21 ml of a 4 N HCl solution was added to an aqueous sodium hyaluronate solution to adjust pH thereof to 3.0, and heating was performed in 80° C. water for 30 minutes. As a result, 8.5 g of sodium hyaluronate was obtained.

Figure 3:
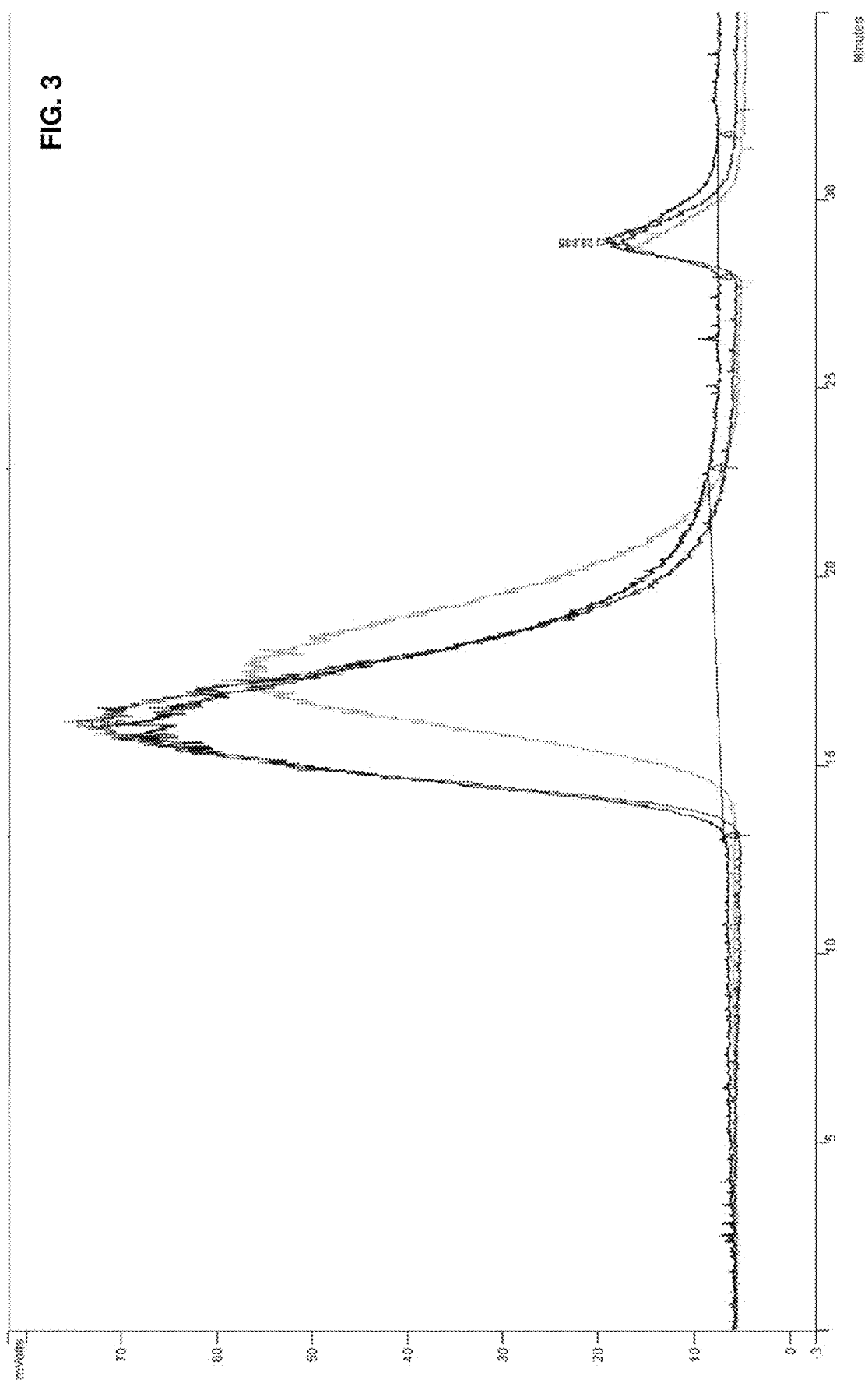
FIG. 3 is an HPLC chromatogram illustrating a molecular weight distribution of low-molecular weight sodium hyaluronate prepared according to each of Examples 6 and 7 of the present invention (blue: a standard molecular weight of 200,000 Daltons, red: Example 6, green: Example 7).

FIG. 3 shows that a molecular weight distribution of sodium hyaluronate obtained according to Example 6 (red peak) almost overlaps a standard molecular weight of 200,000 Daltons (blue peak), and an average molecular weight of sodium hyaluronate obtained according to Example 7 (green peak) is smaller than a standard molecular weight of 200,000 Daltons (blue peak).

Comparative Example 1

1 g of commercially available cosmetic-grade sodium hyaluronate (manufactured by Bloomage Freda Biopharm., molecular weight: 500,000 to 1200,000 Daltons) was dissolved in 100 ml of distilled water to prepare an aqueous 1.0% (w/v) solution. 0.62 ml of 4 N HCl was added to the 1.0% (w/v) aqueous solution to adjust pH thereof to 2.0, followed by being bathed in 90° C. water for 15 minutes. Next, the temperature of the bathed mixture was lowered to room temperature in cold water, and then a 4 N NaOH solution was added thereto to adjust pH thereof to 6.5, followed by adding 400 ml of anhydrous ethanol thereto such that a precipitate was generated. The generated precipitate was filtered, and then dried at 50° C., thereby obtaining 7.3 g of sodium hyaluronate.

Comparative Example 2

An experiment was carried out in the same manner as in Comparative Example 1, except that heating was performed in 90° C. water for 30 minutes. As a result, 6.9 g of sodium hyaluronate was obtained.

Comparative Example 3

An experiment was carried out in the same manner as in Comparative Example 1, except that 0.18 ml of a 4 N HCl solution was added to an aqueous sodium hyaluronate solution to adjust pH thereof to 4.0, and heating was performed in 90° C. water for 30 minutes. As a result, 9.3 g of sodium hyaluronate was obtained.

Figure 4:
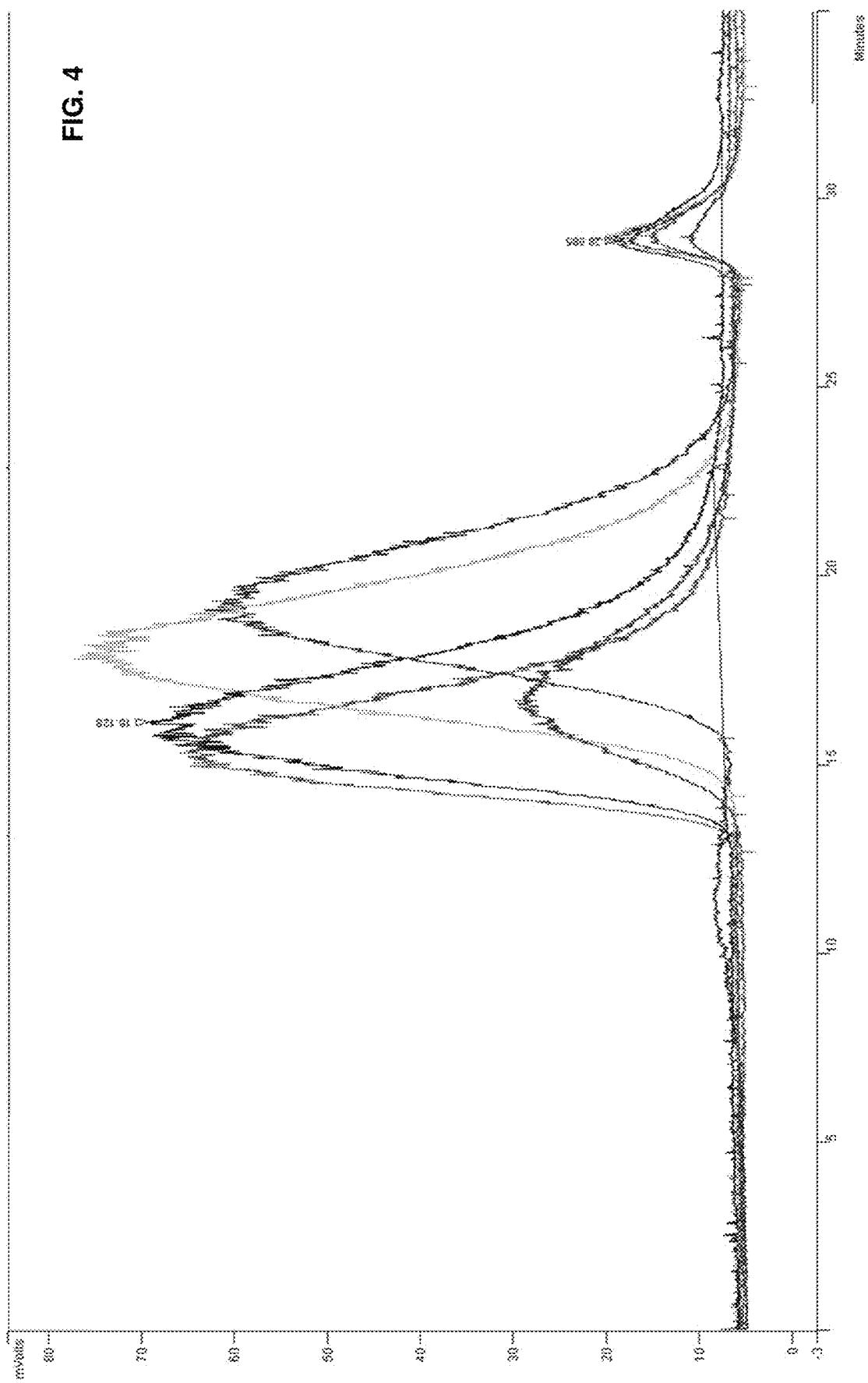
FIG. 4 is an HPLC chromatogram illustrating a molecular weight distribution of sodium hyaluronate prepared according to each of Comparative Examples 1 to 3 (blue: a standard molecular weight of 200,000 Daltons, red: a standard molecular weight of 100,000 Daltons, green: Comparative Example 1, black: Comparative Example 2, pink: Comparative Example 3).

FIG. 4 shows that a molecular weight of sodium hyaluronate obtained according to each of Comparative Example 1 (green peak), Comparative Example 2 (black peak), and Comparative Example 3 (pink peak) is smaller than a standard molecular weight of 100,000 Daltons (red peak).

Comparative Example 4

An experiment was carried out in the same manner as in Comparative Example 1, except that 0.21 ml of a 4 N HCl solution was added to an aqueous sodium hyaluronate solution to adjust pH thereof to 3.0 and heating was performed in 70° C. water for 30 minutes. As a result, 9.1 g of sodium hyaluronate was obtained.

Comparative Example 5

An experiment was carried out in the same manner as in Comparative Example 1, except that 0.21 ml of a 4 N HCl solution was added to an aqueous sodium hyaluronate solution to adjust pH thereof to 3.0 and heating was performed in 100° C. water for 15 minutes. As a result, 7.8 g of sodium hyaluronate was obtained.

Comparative Example 6

An experiment was carried out in the same manner as in Comparative Example 5, except that heating was performed in 100° C. water for 30 minutes. As a result, 7.4 g of sodium hyaluronate was obtained.

Figure 5:
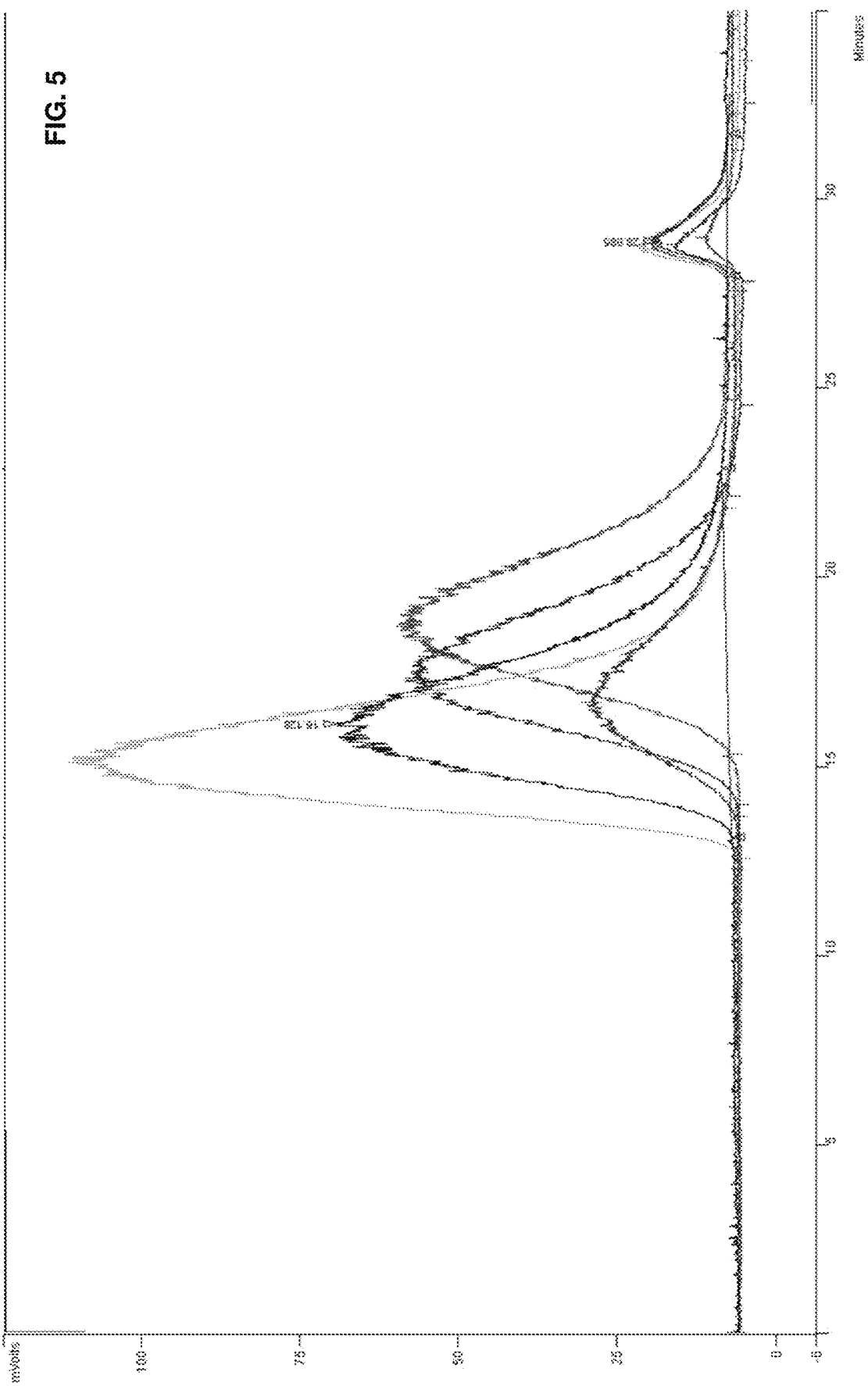
FIG. 5 is an HPLC chromatogram illustrating a molecular weight distribution of sodium hyaluronate prepared according to each of Comparative Examples 4 to 6 of the present invention (blue: a standard molecular weight of 200,000 Daltons, red: a standard molecular weight of 100,000 Daltons, green: Comparative Example 4, black: Comparative Example 5, pink: Comparative Example 6).

FIG. 5 shows that a molecular weight of sodium hyaluronate obtained according to each of Comparative Example 4 (green peak), Comparative Example 5 (black peak), and Comparative Example 6 (pink peak) is smaller than a standard molecular weight of 100,000 Daltons (red peak).

EXPERIMENTAL EXAMPLE

Experimental Example 1

Molecular Weight Distribution Investigation Using FFF-MALS

Each of sodium hyaluronate prepared according to Example 4 and commercially available cosmetic-grade sodium hyaluronate prepared according to Comparative Example 7 (manufactured by Bloomage Freda Biopharm., molecular weight: 500,000 to 1200,000 Daltons) was dissolved in distilled water, thereby preparing an aqueous 1.0% (w/v) solution. A molecular weight distribution of the prepared aqueous 1.0% (w/v) solution was analyzed using a flow field-flow fraction/multi-angle light scattering (FFF/MALS) instrument (manufactured by Wyatt Technology). Results are summarized in Table 1 below.

Analysis conditions were as follows:

Spacer thickness: 250 μm

Membrane: Composite Regenerated Cellulose 20 kDa (Millipore)

Injection amount: 20 μg

Sample concentration: 1 mg/ml

Carrier solution: 0.1 M $NaNO_3$+0.02% $NaN_3$

Sample flow rate: 0.1 mL/min

Cross flow rate: 2.0 mL/min for 0 to 4 minutes; 0.5 mL/min for 4 to 5 minutes; 0.1 mL/min for 5 to 6 minutes; 0.02 mL/min for 6 to 8 minutes

TABLE 1

| | Weight average molecular weight (g/mol) | Number average molecular weight (g/mol) | Plural diversity | Rw (nm) | Rn (nm) |
|---|---|---|---|---|---|
| Example4 | $(1.98 \pm 0.43) \times 10^5$ | $(1.54 \pm 0.40) \times 10^5$ | 1.09 ± 0.02 | 500.4 ± 35.4 | 494.2 ± 34.2 |
| Example7 | $(1.05 \pm 0.08) \times 10^6$ | $(9.13 \pm 2.25) \times 10^5$ | 11.90 ± 3.26 | 213.1 ± 10.2 | 151.8 ± 16.6 |

As shown in Table 1, it was analyzed that, while an average molecular weight of sodium hyaluronate of Example 4 of the present invention was 160,000 Daltons, an average molecular weight of general sodium hyaluronate of used as a raw material for cosmetics (Comparative Example 7) was 1,000,000 Daltons.

Experimental Example 2

Molecular Weight Investigation Using HPLC

A molecular weight of hyaluronate prepared according to each of Examples 1 to 7 and Comparative Examples 1 to 6 was investigated using an HPLC analyzer (Varian Prostar 210 Solvent Delivery System). 10 mg of each sample of hyaluronate prepared according to each of Examples 1 to 7 and Comparative Examples 1 to 6 and reference substances (manufactured by Life Core, 100 kDa and 200 kDa products) was weighed and dissolved in 10 ml of a mobile phase, followed by being filtered through a 0.45 μm filter and being analyzed. Results are shown in FIGS. 1 to 6.

Analysis conditions were as follows:

Column: 1) Ultrahydrogel 1000, 12 μm, 7.8×300 mm, 2K-4M column/2) Ultrahydrogel 500, 10 μm, 7.8×300 mm, 10K-400K column, tandem connection (tandem connection)

Column oven: Room temperature

Flow rate: 0.8 ml/min

Injection volume: 100 μl

Detector: Alltech ELSD 3300

Gas flow: 1 L/min, temperature: 70° C.

Mobile phase: 20 mM-ammonium carbonate (pH 7.8)

Molecular weight reference substance: 200 kDa, 100 kDa HA

Experimental Example 3

Moisture Content Determination Through Limiting Viscosity Measurement

To investigate a moisture content dependent upon molecular weight, the following tests were performed according to a method of measuring a limiting viscosity of sodium hyaluronate disclosed in the European Pharmacopoeia.

As a viscometer, an Ubbelohde-type viscometer was used. Each of sodium hyaluronate prepared according to each of Examples 4 and 5 and Comparative Example 7 and reference substances (manufactured by Lifecore, hyaluronic acid having a molecular weight of 20 kDa, 10 kDa, or 5 kDa) ($M_{Op}$) was added to 10.0 g of a buffer solution ($M_{OS}$) and shaken at 4° C. for 24 hours, followed by being filtered through a glass filter to use as a test liquid ($T_0$). 50 g of a buffer solution was added to 10 g of the test liquid ($T_0$) and shaken at 25° C. for 20 minutes, followed by being filtered through a glass filter. 5 ml of a first filtrate was discarded, and a remaining filtrate was used as Test solution ($T_1$). 5 g of a buffer solution was added to 15 g of Test solution ($T_1$), and Test solution $T_2$ was prepared in the same manner as above. 10 g of a buffer solution was added to 10 g of test liquid ($T_1$), and Test solution $T_3$ was prepared in the same manner as above. 15 g of a buffer solution was added to 5 g of Test solution ($T_1$), and Test solution $T_4$ was prepared in the same manner as above.

A test liquid was fed into the viscometer until the level of the test liquid reached between two marks of sphere A. The viscometer was vertically placed in a thermostatic bath at a temperature (0.1° C.) specified by each veterinary medicine regulation such that sphere D was completely submerged in water, and it was allowed to stand for about 20 minutes until the temperature of the test liquid reached the specified temperature. Tube M was blocked with fingers to prevent air bubbles from entering into tube N, and an upper end of tube N was gently suctioned to pull the level of the test liquid up to the center of sphere D. When the level of the test liquid was reached the center of sphere D, the suction was stopped, an inlet of tube M was opened, and an inlet of tube N was immediately blocked. After confirming that a liquid column at a bottom of the capillary tube was broken, the inlet of tube N was opened to measure a time t (seconds) for the liquid to flow from a top line of sphere C to a bottom line thereof.

1. Viscosity Measurement method: Viscosity measurement method using capillary tube As a method of measuring the viscosity of a Newtonian liquid, a time t(s) for a certain volume of liquid to flow through a capillary tube was measured, and a kinematic viscosity v was calculated according to Equation 1 below.

$$v = K \cdot t \quad \text{[Equation 1]}$$

To find the viscosity η, the density ρ (g/mL) of the liquid at the same temperature was measured and calculated according to Equation 2 below:

$$\eta = v \cdot \rho = K \cdot t \cdot \rho \quad \text{[Equation 2]}$$

In Equations 1 and 2, K (mm$^2$/s$^2$) is an integer of a viscometer and was previously determined using a standard liquid for viscometer calibration. A limiting viscosity represents a diffusion degree of a polymer in a liquid (test liquid) and may be a standard for a molecular weight. The time t for a test liquid at concentration c (g/dL) to flow down and the time $t_0$ for a solvent to flow down were measured, and limiting viscosity [η] was calculated according to Equation 3 below:

$$[\eta] = \lim \left( \frac{\left(\frac{t}{t_0}\right) - 1}{c} \right), c \to 0 \quad \text{[Equation 3]}$$

2. Buffer solution: 0.15 M sodium chloride in sodium phosphate buffer solution, pH 7.0.

Solution A: Prepared by dissolving 1.56 g of $NaH_2PO_4$ and 9.0 g of NaCl in 1 L of distilled water Solution B: Prepared by dissolving 3.58 g of $Na_2HPO_4$ and 9.0 g of NaCl in 1 L of distilled water Solution A was mixed with Solution B until pH reached 7.0, followed by filtration through a glass filter 3. Validation of experiment Times for test liquids $T_1$, $T_2$, $T_3$, and $T_4$ and a buffer solution to flow down a capillary viscometer at 25° C. were respectively measured and expressed as $t_1$, $t_2$, $t_3$, $t_4$, and $t_0$. The same viscometer was used in all tests, and all test liquids were subjected to three measurements. When a deviation of three measurement values was within 0.35% of an average value and $t_1$ was 1.6 to 1.8 times $t_0$, the value was determined to be valid. When a suitable result was not obtained, a buffer solution and test liquids were prepared and tested again.

Limiting viscosity values obtained according to the above experiments are summarized in Table 2 below:

TABLE 2

| Sodium hyaluronate | Limiting viscosity (m$^3$/kg) |
|---|---|
| Example 4 | 0.32 |
| Example 5 | 0.25 |
| Comparative Example 7 | 1.97 |
| 20 kDa (Lifecore) | 0.08 |
| 10 kDa (Lifecore) | 0.03 |
| 5 kDa (Lifecore) | 0.02 |

As shown in Table 2, it can be confirmed that limiting viscosity value is decreased with decreasing molecular weight. From this result, it can be confirmed that a moisture containment ability is decreased with decreasing molecular weight.

Experimental Example 4

Skin Penetration Test Using Animal Models

Fluorescent dye (Flamma 496-dichlorotriazine, Flamma 648-dichlorotriazine) was attached to sodium hyaluronate prepared according to Example 4, hyaluronic acid having a molecular weight of 200 kDa manufactured by Lifecore as a control, and commercially available cosmetic-grade sodium hyaluronate according to Comparative Example 7 (manufactured by Bloomage Freda Biopharm., molecular weight: 500,000 to 1200,000 Daltons). Balb/c-nude mice (male, 5-weeks old, 14 mice) were subjected for a skin penetration test. A test method thereof was as follows:

1. Measurement equipment

IVIS Spectrum (manufacturer: Perkin Elmer, product No.: 124262)

Two Photon Microscopy (manufacturer: Leica Microsystems)

2. Drug labeling with fluorescence a. Each of samples prepared according to Example 4 and Comparative Example 7 and a control was diluted with PBS at a concentration of 12.5 μg/ml.

b. Fluorescent dye (Flamma 496-dichlorotriazine, Flamma 648-dichlorotriazine) was dissolved in DMSO at a concentration of 1 mg/ml. This mixture was prepared immediately before reaction and was used immediately.

c. 20 μL of the fluorescent dye solution of the process b was added to 1 mL to the drug solution of the process a.

d. The resultant mixture was incubated at room temperature for 2 hours while flipping up and down every 15 minutes.

3. Investigation of skin penetration of drugs using optical imaging

IVIS Spectrum was measured immediately, 30 minutes, 1 hour, 2 hours, 6 hours, and 24 hours after applying 10 μL (10 μg/ml) of a fluorescent dye-labeled sample of each of Example 4 according to the present invention, a control, and Comparative Example 7 to the back of a Balb/c-nude mouse, and then washing a left side of the mouse with PBS after 15 minutes and washing a right side of the mouse with PBS after 30 minutes to remove residues. Results are shown in FIG. 6.

Figure 6:
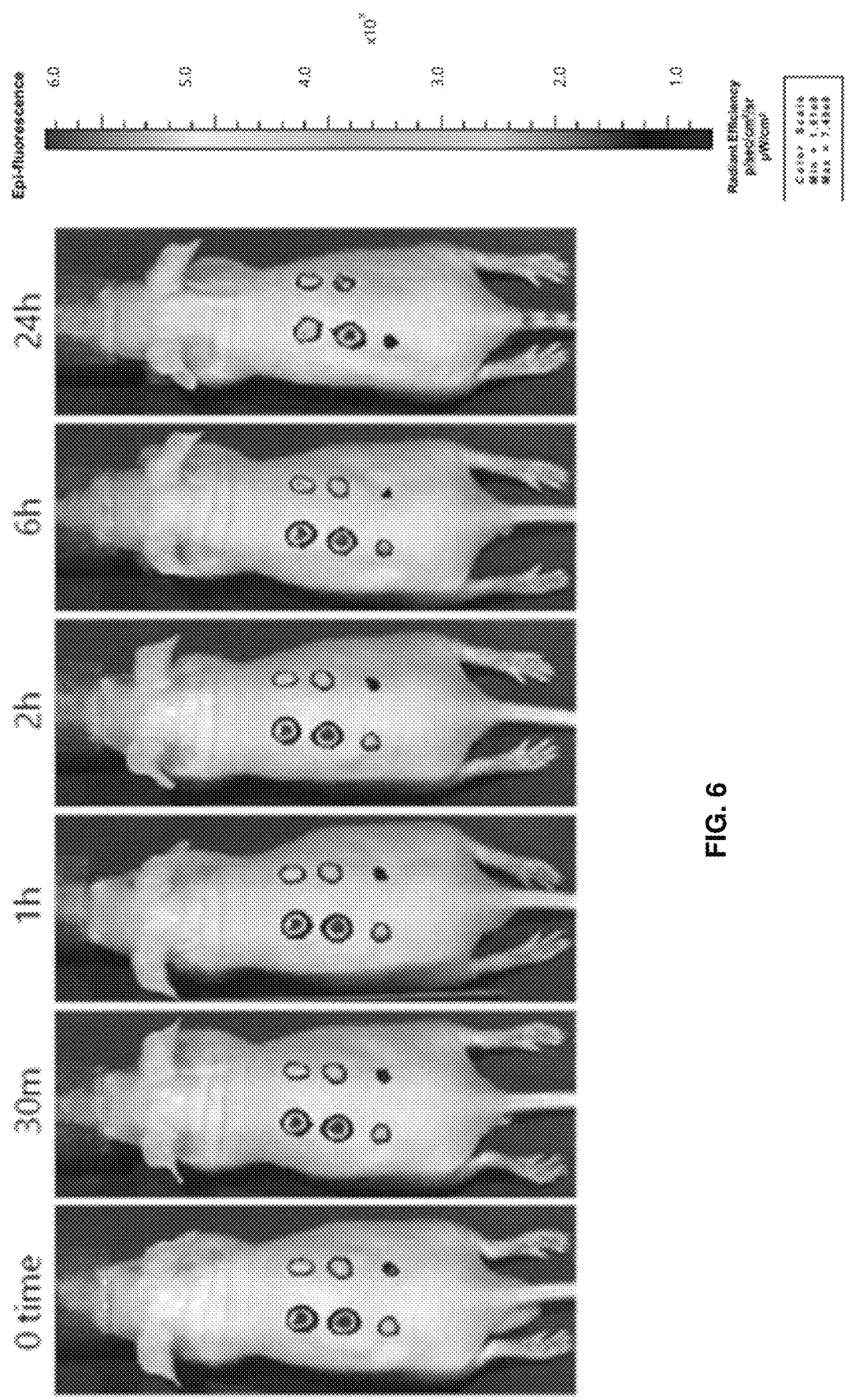
FIG. 6 illustrates results measured using IVIS Spectrum immediately, 30 minutes, 1 hour, 2 hours, 6 hours, and 24 hours after applying 10 μL (10 μg/ml) of a fluorescent dye-labeled sample of each of Example 4 according to the present invention, a control, and Comparative Example 7 to the back of a Balb/c-nude mouse, and then washing a left side of the mouse with PBS after 15 minutes and washing a right side of the mouse with PBS after 30 minutes to remove residues.

As shown in FIG. 6, it was confirmed that the control and the sample of Example 4 penetrated the skin more efficiently after 30 minutes than after 15 minutes. However, it was confirmed that the sample of Comparative Example 7 was washed away without penetrating the skin because the molecular weight thereof was larger than that of the sample of Example 4.

4. Investigation of skin penetration of drugs using two-photon microscopy (TPM)

10 μL (10 μg/ml) of a fluorescent dye-labeled sample of each of Example 4 according to the present invention, a control, and Comparative Example 7 was applied to the back of a Balb/c-nude mouse, followed by washing with a PBS buffer after 15 minutes to remove residues. A skin section was collected from the mouse and then fixed with 4% formaldehyde to manufacture an incision specimen. The obtained skin tissue slide was subjected to confocal imaging using a two-photon microscope.

Figure 7:
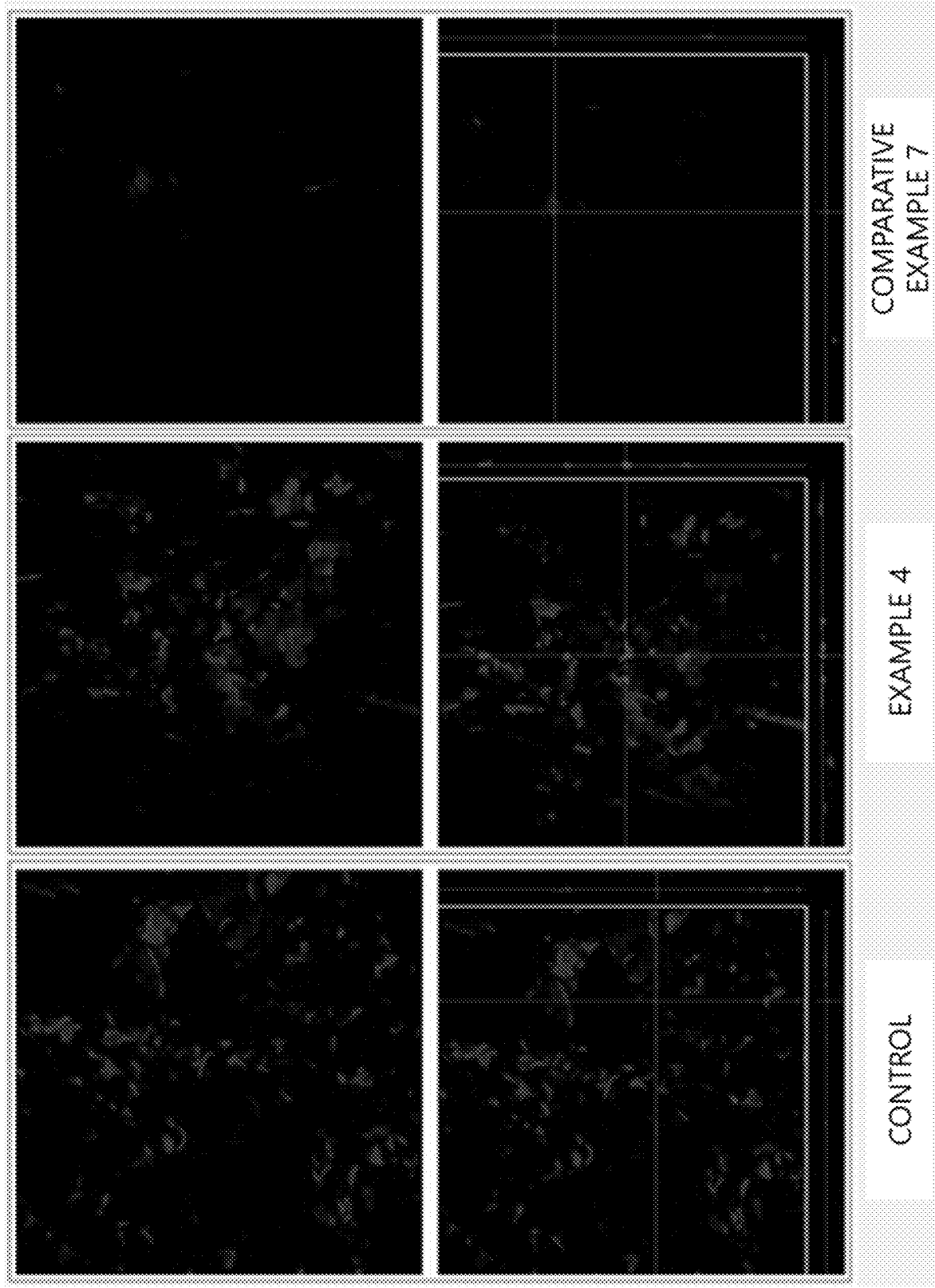
FIG. 7 illustrates confocal imaging results of skin tissue slides measured using a two-photon microscope. In particular, to obtain the skin tissue slides, after applying 10 μL (10 μg/ml) of a fluorescent dye-labeled sample of each of Example 4 according to the present invention, a control, and Comparative Example 7 to the back of a Balb/c-nude mouse and then washing with a PBS buffer after 15 minutes to remove residues, a skin section was collected from the mouse and then fixed with 4% formaldehyde to manufacture an incision specimen.

As shown in FIG. 7, when the skin tissues were cut and drug penetration thereinto was observed using TPM imaging, it was confirmed that the sample of Example 4 and the control penetrated the skin without a significant difference therebetween, but the sample of Comparative Example 7 was almost absent in the skin.

The aforementioned description of the present invention is provided by way of example and those skilled in the art will understand that the present invention can be easily changed or modified into other specified forms without change or modification of the technical spirit or essential characteristics of the present invention. Therefore, it should be understood that the aforementioned examples are only provided by way of example and not provided to limit the present invention. It should be understood that the scope of the present invention is defined by the following claims and the invention is to cover all modifications, equivalents, and alternatives falling within the spirit and scope of the invention as defined by the claims.

The invention claimed is:

1. A method of preparing low-molecular weight hyaluronic acid having a molecular weight of 100,000 to 200,000 Daltons, the method comprising:
    thermally treating, in a range of pH 2.5 to 3.5, an aqueous solution that contains hyaluronic acid having a molecular weight of 500,000 Daltons or greater,
    wherein a hyaluronate acid concentration of the aqueous solution is 1 to 2% (weight/volume), wherein the thermally treating is performed at 80 to 90° C.,
    wherein the thermally treating is performed for 15 to 30 minutes,
    wherein, after the thermally treating, a resultant reaction solution is neutralized with an aqueous alkali metal hydroxide solution to obtain low-molecular weight hyaluronic acid in a form of an alkali metal salt, and
    wherein pH of the reaction solution is adjusted to 6.5 to 7.0.

2. The method according to claim 1, wherein the alkali metal salt is a sodium salt.

3. The method according to claim 1, wherein, after the neutralization, an organic solvent is added to the reaction solution to generate a precipitate, and the precipitate is filtered to obtain a powder-type alkali metal salt of hyaluronic acid.

4. The method according to claim 3, wherein the organic solvent is one or more selected from the group consisting of methanol, ethanol, acetone, and isopropyl alcohol.

5. The method according to claim 3, wherein a volume ratio of the reaction solution: the organic solvent is 1:5 to 1:6.

* * * * *